United States Patent
Bae et al.

(10) Patent No.: US 8,883,086 B2
(45) Date of Patent: Nov. 11, 2014

(54) APPARATUS AND METHOD FOR MEASURING BIOMEDICAL DATA AND MEASUREMENT STRIP

(75) Inventors: Byeong-Woo Bae, Anyang (KR); Sung-Dong Lee, Anyang (KR); Byung-Hoon Kho, Seongnam (KR); Ji-Eon Ryu, Anyang (KR); Jin-Kyeong Kim, Gunpo (KR); Hyou-Arm Joung, Uiwang (KR)

(73) Assignee: Infopia Co., Ltd. (KR)

( * ) Notice: Subject to any disclaimer, the term of this patent is extended or adjusted under 35 U.S.C. 154(b) by 468 days.

(21) Appl. No.: 12/722,252

(22) Filed: Mar. 11, 2010

(65) Prior Publication Data

US 2010/0305419 A1 Dec. 2, 2010

(30) Foreign Application Priority Data

Jun. 2, 2009 (KR) ........................ 10-2009-0048805

(51) Int. Cl.
*G01N 33/52* (2006.01)
*A61B 5/145* (2006.01)
(Continued)

(52) U.S. Cl.
CPC ............ *A61B 5/14546* (2013.01); *G01N 33/49* (2013.01); *A61B 5/14532* (2013.01);
(Continued)

(58) Field of Classification Search
CPC ........... A61B 5/145; A61B 2561/0295; A61B 2560/0431; A61B 2560/0462; G01N 21/00; G01N 21/01; G01N 21/17; G01N 21/8483; G01N 33/49; G01N 33/92; G01N 33/5302; G01N 33/4875; G01N 33/48771; B01L 2300/021; B01L 2300/024; B01L 2300/025; B01L 2300/0816; B01L 2300/0825; B01L 2200/025

USPC .......... 435/287.1, 288.7, 283.1, 287.7, 287.9, 435/288.3, 805, 808, 970; 422/69, 68.1, 422/82.05, 402, 403, 404; 436/501, 71
See application file for complete search history.

(56) References Cited

U.S. PATENT DOCUMENTS

| | | |
|---|---|---|
| 3,907,503 A | 9/1975 | Betts et al. |
| 5,945,341 A | 8/1999 | Howard, III |
| 6,773,671 B1 | 8/2004 | Lewis et al. |

FOREIGN PATENT DOCUMENTS

| | | |
|---|---|---|
| CN | 1964789 A | 5/2007 |
| CN | 101413941 A | 4/2009 |

(Continued)

OTHER PUBLICATIONS

International Search Report; PCT/KR2010/002284; Oct. 27, 2010.

*Primary Examiner* — Melanie Y Brown
*Assistant Examiner* — Erik B Crawford
(74) *Attorney, Agent, or Firm* — Cantor Colburn LLP

(57) ABSTRACT

Disclosed herein are an apparatus and method for measuring biomedical data and a measurement strip. The apparatus includes a plurality of detection units arranged within a strip reception area on a plane and spaced apart from each other, a measurement type determination unit for determining whether reactive portions are present in areas of the measurement strip corresponding to the plurality of detection units based on detection results obtained by the detection units and determining a type of measurement based on results of the determination, a biomedical data measurement unit for activating part or all of the detection units according to the type of measurement determined by the measurement type determination unit, and measuring the biomedical data using the activated detection units, and an output unit for outputting the measured biomedical data to an outside.

8 Claims, 7 Drawing Sheets

(51) Int. Cl.
*G01N 21/00* (2006.01)
*G01N 21/17* (2006.01)
*G01N 33/92* (2006.01)
*G01N 33/487* (2006.01)
*G01N 33/49* (2006.01)
*G01N 21/84* (2006.01)
*A61B 5/1455* (2006.01)

(52) U.S. Cl.
CPC ............... *G01N 21/00* (2013.01); *G01N 21/17* (2013.01); *G01N 33/92* (2013.01); *A61B 2560/0462* (2013.01); *G01N 33/48771* (2013.01); *G01N 21/8483* (2013.01); *A61B 2560/0431* (2013.01); *B01L 2300/025* (2013.01); *B01L 2300/021* (2013.01); *B01L 2300/0825* (2013.01); *B01L 2300/0816* (2013.01); *A61B 5/1455* (2013.01); *B01L 2300/024* (2013.01); *B01L 2200/025* (2013.01); *A61B 2562/0295* (2013.01); *Y10S 435/805* (2013.01); *Y10S 435/808* (2013.01); *Y10S 435/97* (2013.01)
USPC ......... 422/404; 422/69; 422/68.1; 422/82.05; 422/402; 422/403; 435/283.1; 435/287.1; 435/287.7; 435/287.9; 435/288.3; 435/288.7; 435/805; 435/808; 435/970; 436/501; 436/71

(56) References Cited

FOREIGN PATENT DOCUMENTS

| | | | |
|---|---|---|---|
| JP | 11-142338 | A | 5/1999 |
| JP | 2002303625 | A | 10/2002 |
| JP | 2004535576 | A | 11/2004 |
| JP | 2007538230 | A | 12/2007 |
| KR | 1020040013003 | A | 2/2004 |
| KR | 1020060064807 | A | 6/2006 |
| KR | 1020070092097 | A | 9/2007 |
| WO | 9613707 | | 5/1996 |
| WO | 03001964 | A2 | 1/2003 |

APPARATUS AND METHOD FOR MEASURING BIOMEDICAL DATA AND MEASUREMENT STRIP

BACKGROUND OF THE INVENTION

1. Field of the Invention

The present invention relates generally to the measurement of biomedical data, and, more particularly, to an apparatus and method for measuring biomedical data and a measurement strip.

2. Description of the Related Art

Due to the recent increases in geriatric disease and cardiac disorder prevalence rate in the middle-aged, consumers have a growing interest in the measurement of cholesterol and triglyceride.

The amount of total cholesterol within serums, blood plasma or blood has been known as one of the best biomedical data for evaluating a danger of coronary arteriosclerosis. If someone has a doubt about a danger of his or her arteriosclerosis, it would be better to measure the amount of total cholesterol. However, since a recent clinical study has revealed that there is a positive correlation between the amount of Low Density Lipoprotein (LDL) and coronary arteriosclerosis, the measurement of the amount of LDL is more useful than the measurement of the amount of total cholesterol. Furthermore, higher-value triglyceride suggests a danger of atherosclerosis, which may result in a danger of angina pectoris, cardiac infarction or cerebral apoplexy. Accordingly, the measurement of the value of triglyceride is also meaningful.

Such types of biomedical data may be measured using different measuring apparatuses or one measuring apparatus. If a measuring apparatus is required for each type of biomedical data, it will be inefficient and troublesome. In order to measure several types of biomedical data using one measuring apparatus, the measuring apparatus must be informed of the types of measurement. Although a user may set the type of measurement by entering a key, this causes inconvenience to the user.

A scheme in which an electrical resistor, a barcode or an optical code is attached to a measurement strip and a measuring apparatus detects this is possible. However, this scheme entails the increase in cost and the inconvenience in fabrication.

SUMMARY OF THE INVENTION

Accordingly, the present invention has been made keeping in mind the above problems occurring in the prior art, and an object of the present invention is to provide a measuring apparatus and method which enables the type of measurement to be detected without increasing cost and causing inconvenience to a user.

According to an aspect of the present invention, there is provided an apparatus for measuring biomedical data, including a plurality of detection units arranged within a strip reception area on a plane and spaced apart from each other; a measurement type determination unit for determining whether reactive portions are present in areas of the measurement strip corresponding to the plurality of detection units based on detection results obtained by the detection units and determining a type of measurement based on results of the determination; a biomedical data measurement unit for activating part or all of the detection units according to the type of measurement determined by the measurement type determination unit, and measuring the biomedical data using the activated detection units; and an output unit for outputting the measured biomedical data to an outside.

According to an aspect of the present invention, there is provided a measurement strip configured to be inserted into a measuring apparatus and to be used to measure biomedical data, wherein the apparatus has n detection units arranged within a strip reception area of the measuring apparatus, the strip includes (n−1) or less reactive portions spaced apart from each other on a plane according to a type of measurement to correspond to respective positions of the detection units.

According to an aspect of the present invention, there is provided a method of measuring biomedical data in an apparatus for measuring biomedical data using an inserted measurement strip, including determining whether reactive portions are present in areas of the measurement strip corresponding to a plurality of respective detection units based on detection results obtained by the detection units, determining the type of measurement based on results of the determination; and measuring biomedical data based on the type of measurement.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Some embodiments of the present invention will be described in detail with reference to the accompanying drawings.

Figure 1:
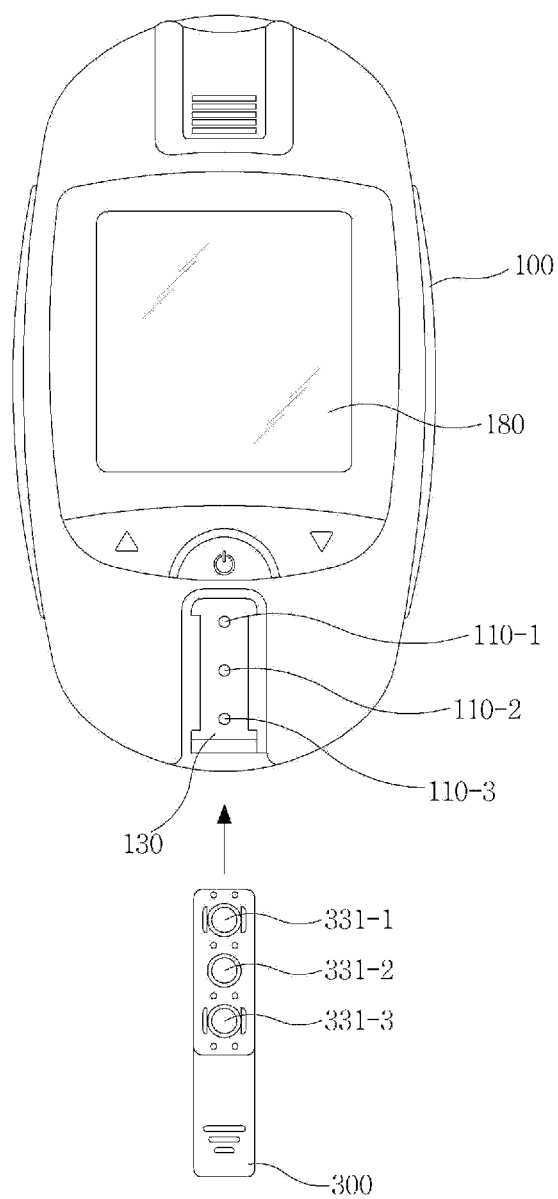
FIG. 1 is a schematic diagram showing an apparatus for measuring biomedical data and a measurement strip according to an embodiment of the present invention.

FIG. 1 is a schematic diagram showing an apparatus for measuring biomedical data and a measurement strip according to an embodiment of the present invention. Referring to FIG. 1, the measurement strip 300 includes an upper support 330 which includes a plurality of reactive portions capable of measuring biomedical data, such as the triglyceride of blood and the amount of cholesterol. The upper support 330 including the reactive portions has target data varying depending on position, which will be described in detail later. Projections are formed on the top of the measurement strip 300 so that the measurement strip 300 can be inserted into a strip reception area 130 with the projections of the measurement strip 300 engaged with the depressions of the strip reception area 130 and with the measurement strip 300 easily fastened within the strip reception area 130.

The apparatus for measuring biomedical data 100 includes a power button, the strip reception area 130, and a display unit 180. The apparatus for measuring biomedical data 100 has a structure in which the depressions are formed in the periphery of the strip reception area 130 so that the measurement strip 300 can be easily inserted and fastened thereinto. The strip reception area 130 includes a plurality of detection units 110 (e.g., 110-1, 110-2, and 110-3) which are formed along the central portion of the strip reception area 130 and which are spaced apart from each other. The plurality of detection units 110 correspond to the reactive portions of the measurement strip 300, respectively. Part or all of the detection units are activated depending on the type of measurement, and detect reactive areas including corresponding reactive portions.

Figure 2:
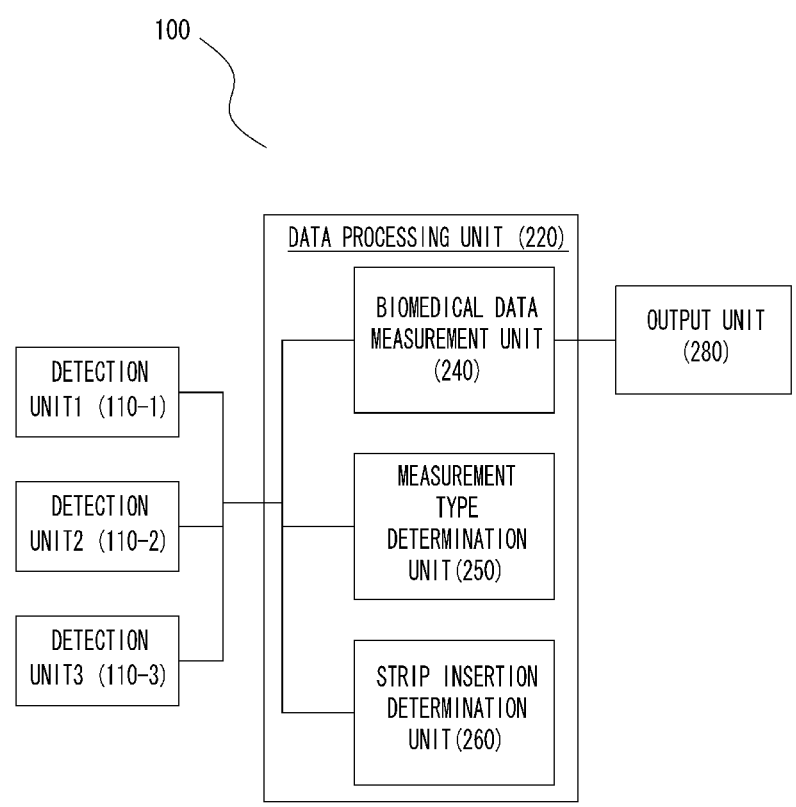
FIG. 2 is a schematic block diagram showing an apparatus for measuring biomedical data according to another embodiment of the present invention.

FIG. 2 is a schematic block diagram showing an apparatus for measuring biomedical data 100 according to another embodiment of the present invention. Referring to FIG. 2, the apparatus for measuring biomedical data 100 includes a plurality of detection units 110 (e.g., 110-1, 110-2, and 110-3), a data processing unit 220, and an output unit 280. The data processing unit 220 includes a biomedical data measurement unit 240 and a measurement type determination unit 250.

The detection units 110 detect respective reactive areas of the measurement strip corresponding to the detection units 110. The detection units 110 are generally implemented to measure the reflectance of the reactive areas of the measurement strip corresponding to the detection units 110. Each of the detection units 110 may be configured to include a light-emitting unit and a light-receiving unit. The light-emitting unit of each detection unit may include a Light-Emitting Diode (LED) for generating light and a drive circuit, while the light-receiving unit of the detection unit may include a photodiode for absorbing light and an analog-to-digital converter. The detection unit receives light reflected from a corresponding reactive area on the measurement strip, converts the amount of received light into a digitized electrical signal value, and sends the digital signal to the biomedical data measurement unit 240, the measurement type determination unit 250, and a strip insertion determination unit 260.

The measurement type determination unit 250 determines whether reactive portions are present in the reactive areas of the measurement strip 300 corresponding to the respective detection units 110 based on results detected by the plurality of detection units 110, and then determines the type of measurement based on the results of the determination. According to an embodiment, each reactive portion of the measurement strip 300 may include white reactive paper. If the amount of light received from one detection unit is lower than a first reference value, the measurement type determination unit 250 determines a reactive portion not to be present in the reactive area of the measurement strip corresponding to the corresponding detection unit. If the amount of light received from one detection unit is larger than the first reference value, the measurement type determination unit 250 determines that a reactive portion is present in the reactive area of the measurement strip corresponding to the corresponding detection unit. The type of measurement performed by the biomedical data measuring apparatus may be the measurement of the amount of total cholesterol, the measurement of the amount of High Density Lipoprotein (HDL) cholesterol, and/or the measurement of the amount of triglyceride.

The biomedical data measurement unit 240 activates part or all of the detection units 110 according to the type of measurement determined by the measurement type determination unit 250, and measures biomedical data based on detection results obtained by the detection units 110.

The output unit 280 outputs measured biomedical data to the outside. In an embodiment, the output unit 280 may be a liquid crystal display or a 7-segment display. In another embodiment, the output unit 280 may be a voice synthesis and output unit which outputs a measured value in the form of voice. In yet another embodiment, the output unit 280 may be an interface, such as a Universal Serial Bus (USB), which outputs a measured value to an external device, such as a mobile phone.

According to an additional embodiment of the present invention, the data processing unit 220 may further include the strip insertion determination unit 260. When the detection units 110 detect the corresponding reactive areas of the measurement strip and send detection results to the strip insertion determination unit 260, the strip insertion determination unit 260 receives the detection results from the detection units 110. As an example, the reactive portion of the measurement strip may include white reactive paper, and the measurement strip may include at least one reactive portion. If the amount of light received from the detection units is determined to fall within the range of the amounts of light which can be received when a reactive portion is present, the strip insertion determination unit 260 determines the measurement strip to have been appropriately inserted into the strip reception area 130.

Figure 3A:
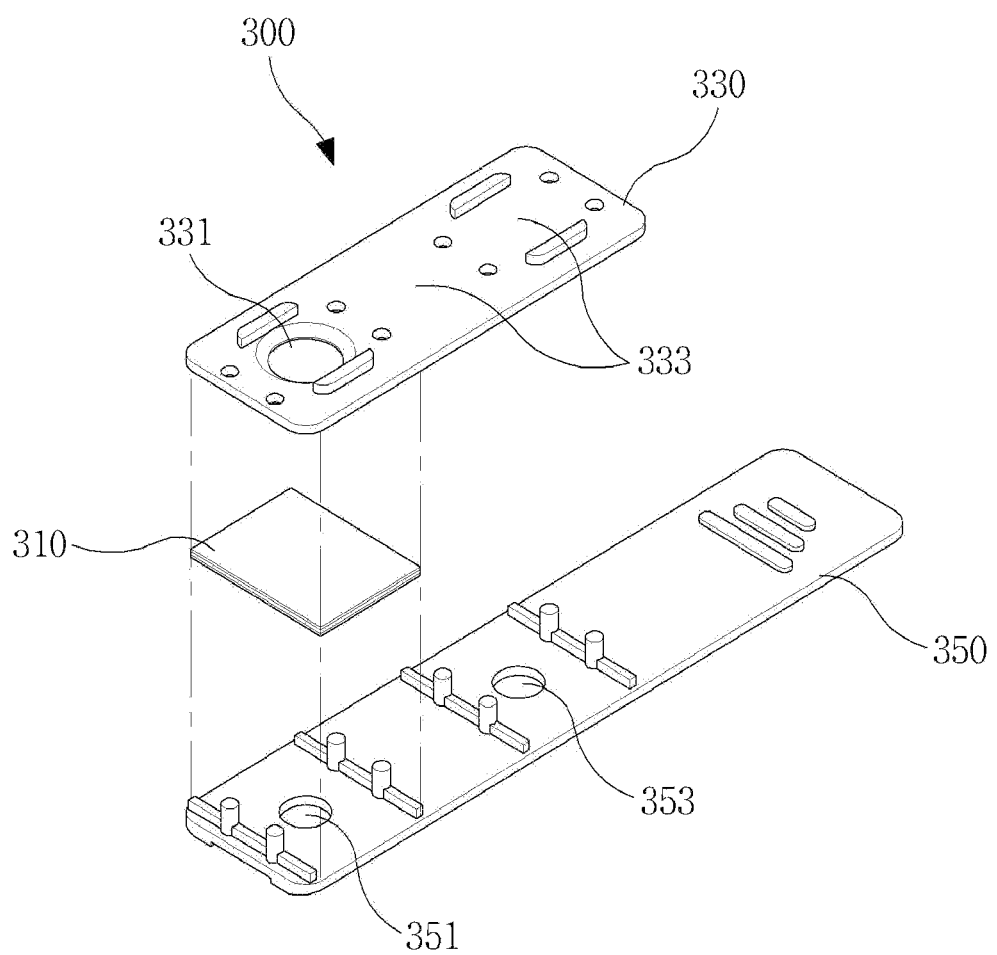
FIGS. 3A and 3B are exploded perspective views showing measurement strips according to further embodiments of the present invention.
Figure 3B:
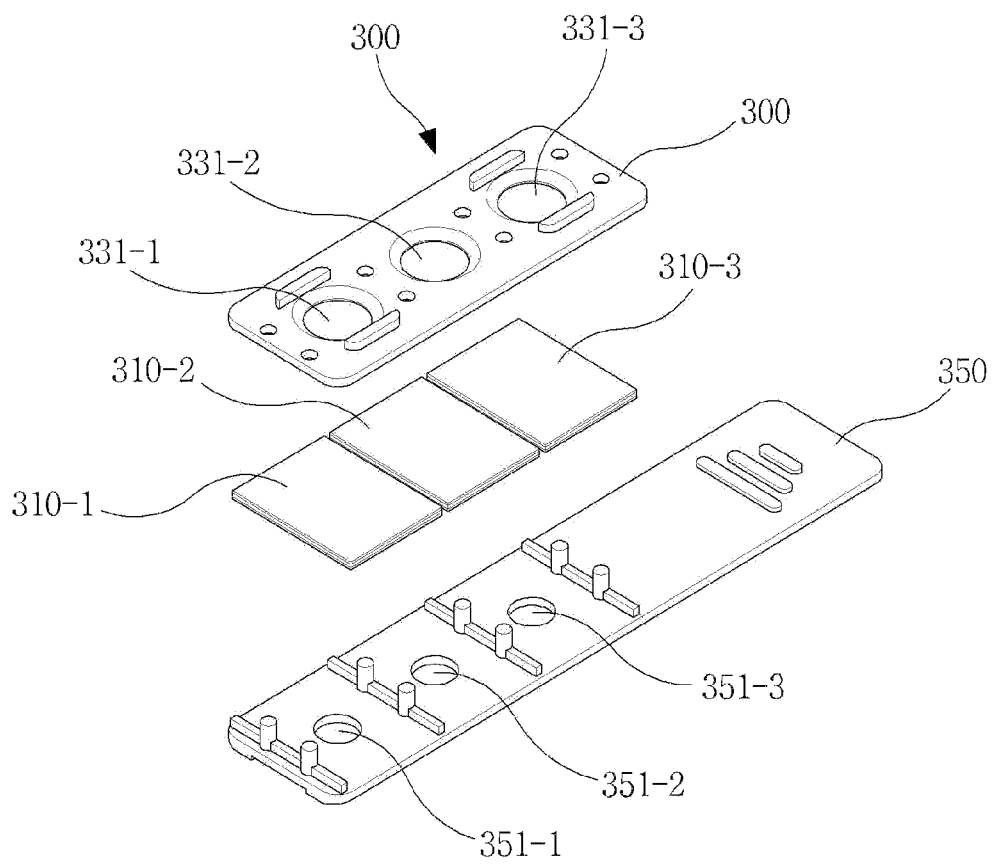

FIGS. 3A and 3B are exploded perspective views showing measurement strips 300 according to further embodiments of the present invention. FIG. 3A is an exploded perspective view showing a measurement strip in which one reactive area is present, and FIG. 3B is an exploded perspective view showing a measurement strip in which three reactive areas are present. In FIGS. 3A and 3B, the reactive portions 310 (e.g., 310-1, 310-2, and 310-3) are arranged in a straight line to correspond to the respective detection units of the biomedical data measuring apparatus, and are spaced apart from each other at regular intervals.

Referring to FIG. 3A, the measurement strip 300 includes an upper support 330, a lower support 350, and at least one reactive portion 310. Biologic reactions actually occur in the reactive portions 310 of the measurement strip 300. Upper holes 331 are formed in the upper support 330 to correspond to the respective reactive portions 310. Each of the upper holes 331 is used to enable a body fluid to be supplied to a corresponding reactive portion 310 and to cause a biologic reaction to occur therein. The upper portions 333 of the upper support 330 including no reaction units are not open, thereby causing detection results to be different from detection results for the portion including the reaction unit.

The lower support 350 includes two or more first lower holes 351 and second lower holes 353. The hole 351 formed in a portion where the reactive portion 310 is placed is used such that a corresponding detection unit can detects the results of a reaction in the reactive portion 310. The second lower hole 353 formed in a portion where the reactive portion is not placed is used to emphasize the difference between detection results in this portion and detection results in the portion where the reactive portion is placed.

Figure 4:
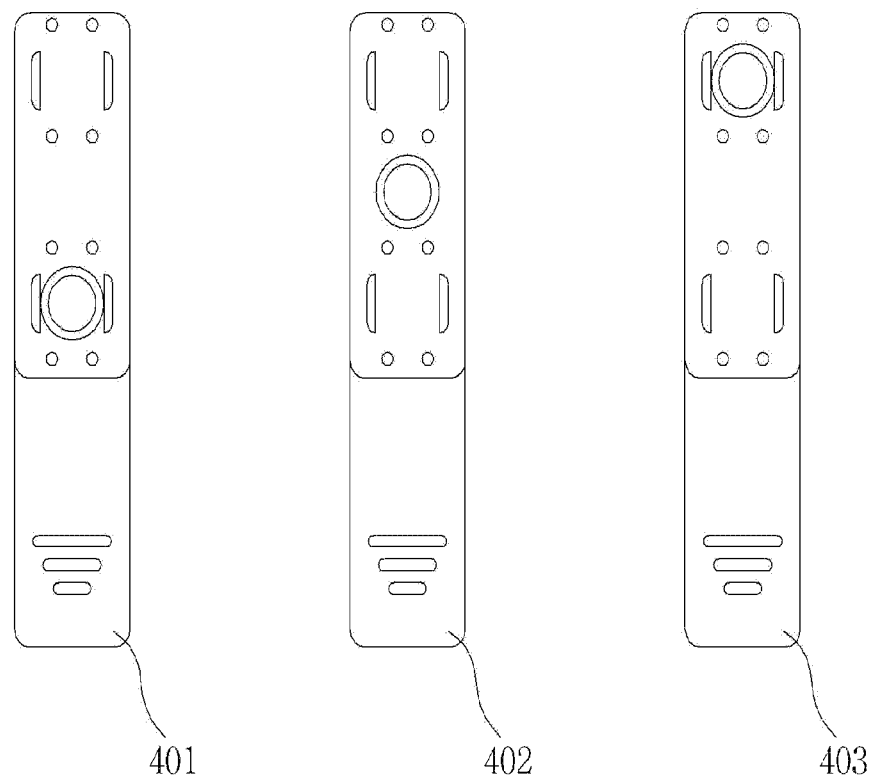
FIG. 4 is a front view showing measurement strips according to further embodiments of the present invention.

FIG. 4 is a front view showing measurement strips according to further embodiments of the present invention. The measurement strip of FIG. 4 has a construction similar to that of FIG. 3A.

Referring to FIG. 4, each of the measurement strips may have a reactive portion at a position varying according to the type of measurement. For example, assuming that the types of measurement are the measurement of the amount of total cholesterol, the measurement of the amount of HDL cholesterol and the measurement of the amount of triglyceride, a construction for measuring the amount of total cholesterol may be that of a measurement strip 1 401, a construction for measuring the amount of HDL cholesterol ma be that of a measurement strip 2 402 and a construction for measuring the amount of triglyceride may be that of a measurement strip 3 403.

Furthermore, at least one of the top cover and lower support 350 of the measurement strip 300 may have a different color according to the type of measurement. According to an embodiment, the top cover and lower support of the measurement strip which are fabricated using one mold have the same color. Furthermore, assuming that the types of measurement are the measurement of the amount of total cholesterol, the measurement of the amount of HDL cholesterol and the measurement of the amount of triglyceride, the top cover and lower support of the measurement strip for measuring the amount of total cholesterol may have red color, the top cover and lower support of the measurement strip for measuring the amount of triglyceride may have green color, and the top cover and lower support of the measurement strip for measuring the amount of HDL cholesterol may have blue color. This offers an advantage in that a user can easily distinguish the measurement strips.

Figure 5:
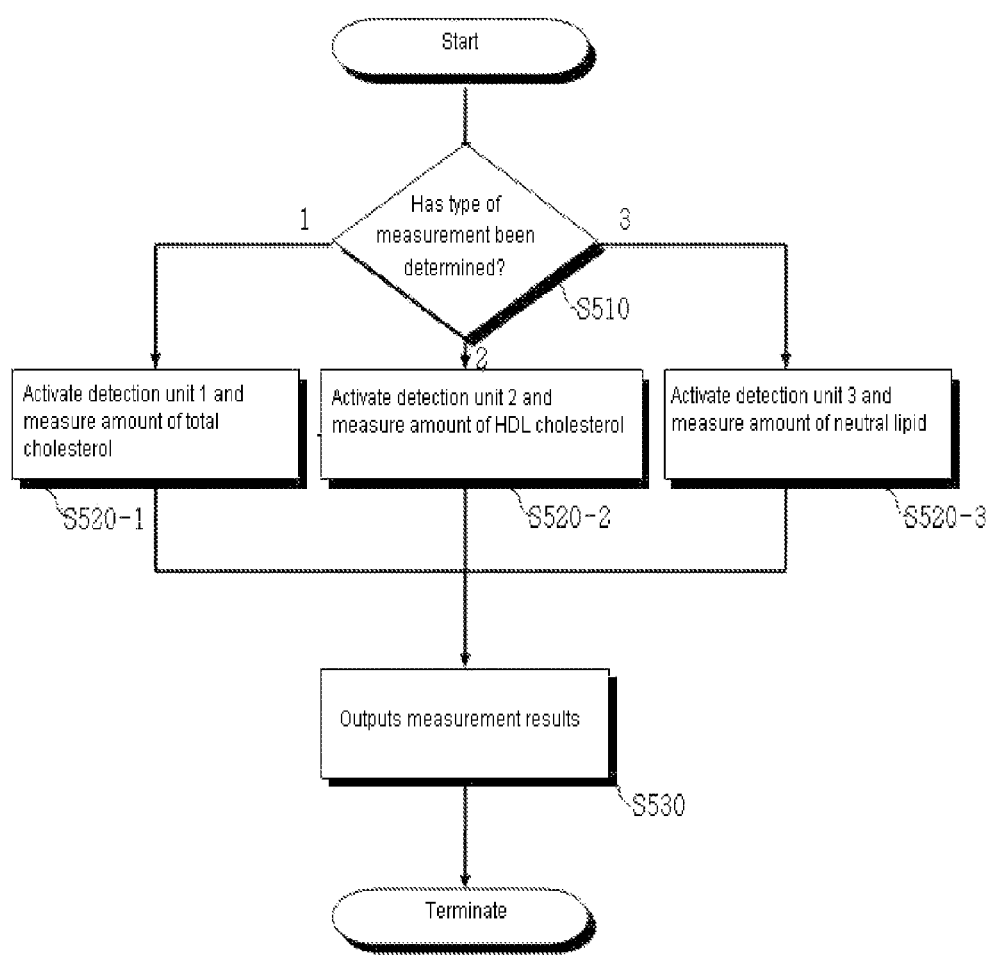
FIG. 5 is a flowchart illustrating a method of measuring biomedical data which is performed in the apparatus for measuring biomedical data according to still another embodiment of the present invention.

FIG. 5 is a flowchart illustrating a method of measuring biomedical data which is performed in the apparatus for measuring biomedical data according to still another embodiment of the present invention.

Referring to FIG. 5, when the measurement strip is inserted into the strip reception area 130 of the apparatus for measuring biomedical data, the plurality of detection units detects the respective reactive areas of the measurement strip, and sends detection results to the measurement type determination unit 250. The measurement type determination unit 250 determines whether the reactive portions are present in the respective reactive areas based on the detection results, and determines the type of measurement based on the results of the determination at step S510. Thereafter, the biomedical data measurement unit 240 activates part or all of the detection units based on the type of measurement, and measures biomedical data using the activated detection units. For example, it is assumed that the types of measurement are the measurement of the amount of total cholesterol, the measurement of the amount of HDL cholesterol and the measurement of the amount of triglyceride in the apparatus for measuring biomedical data, including three detection units 1, 2, and 3. If the type of measurement is 1, the detection unit 1 may be activated in order to measure the amount of total cholesterol at step S520-1. If the type of measurement is 2, the detection unit 2 may be activated in order to measure the amount of HDL cholesterol at step S520-2. If the type of measurement is 3, the detection unit 3 may be activated in order to measure the amount of triglyceride at step S520-3. Biomedical data generated based on the measurement are sent to the output unit 280. The output unit 280 outputs the biomedical data as measurement results to the outside at step S530.

Figure 6:
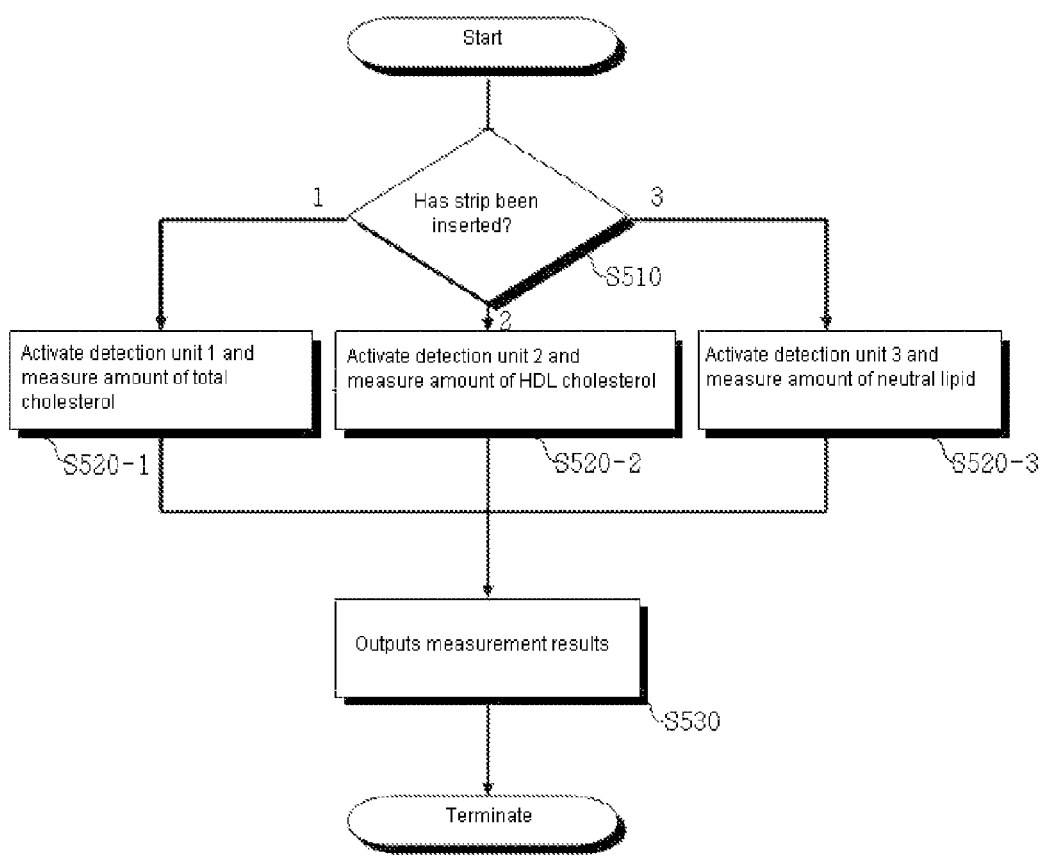
FIG. 6 is a flowchart illustrating a method of measuring biomedical data which is performed in the apparatus for measuring biomedical data according to still another embodiment of the present invention.

FIG. 6 is a flowchart illustrating a method of measuring biomedical data which is performed in the apparatus for measuring biomedical data according to still another embodiment of the present invention. The method of FIG. 6 further includes the step of determining whether the measurement strip has been inserted before determining the type of measurement, as compared with that of FIG. 5.

Referring to FIG. 6, when the measurement strip is inserted into the strip reception area 130 of the apparatus for measuring biomedical data, the plurality of detection units detects the respective reactive areas of the measurement strip, and sends detection results to the strip insertion determination unit 260 and the measurement type determination unit 250. The strip insertion determination unit 260 determines whether the measurement strip has been inserted based on the detection results at step S605. If, as a result of the determination, the measurement strip is determined not to have been inserted, the strip insertion determination unit 260 terminates the process. If, as a result of the determination, the measurement strip is determined to have been inserted, the type of measurement is determined. The measurement type determination unit 250 determines whether the reactive portions are present in the respective reactive areas based on the detection results and determines the type of measurement based on the results of the determination at step S610. Thereafter, the biomedical data measurement unit 240 activates part or all of the detection units based on the type of measurement, and measures biomedical data using the activated detection units. For example, it is assumed that the types of measurement are the measurement of the amount of total cholesterol, the measurement of the amount of HDL cholesterol, and the measurement of the amount of triglyceride in the apparatus for measuring biomedical data, including three detection units 1, 2, and 3. If the type of measurement is 1, the detection unit 1 may be activated in order to measure the amount of total cholesterol at step S620-1. If the type of measurement is 2, the detection unit 2 may be activated in order to measure the amount of HDL cholesterol at step S620-2.

If the type of measurement is 3, the detection unit 3 may be activated in order to measure the amount of triglyceride at step S620-3. Biomedical data generated based on the measurement are sent to the output unit 280. The output unit 280 outputs the biomedical data as measurement results to the outside at step S630.

As described above, the apparatus for measuring biomedical data according to the present invention can distinguish the types of measurement from each other and determine whether a measurement strip has been inserted without requiring additional elements such as barcode and electrodes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:
1. An apparatus for measuring biomedical data, comprising:
   a plurality of detection units configured to respectively correspond to predetermined areas of a measurement strip;
   a measurement type determination unit for determining whether reactive portions are present in each of the predetermined areas of the measurement strip corresponding to the plurality of detection units based on detection results obtained by the detection units and determining a type of measurement based on the presence of the reactive portion in each of the predetermined areas of the measurement strip;
   a biomedical data measurement unit for activating at least one detection unit corresponding to the type of measurement determined by the measurement type determination unit among the plurality of detection units, and measuring the biomedical data using the activated detection units; and
   an output unit for outputting the measured biomedical data to an outside.

2. The apparatus as set forth in claim 1, further comprising a strip insertion determination unit for determining whether the measurement strip has been inserted based on the detection results obtained by the plurality of detection units.

3. The apparatus as set forth in claim 1, wherein the output unit is a display unit for displaying the biomedical data on a screen.

4. The apparatus as set forth in claim 1, wherein each of the plurality of detection units comprises:
    a light-emitting unit for emitting light toward a reactive portion of the measurement strip; and
    a light-receiving unit for detecting a reflectance of the reactive portion of the measurement strip.

5. The apparatus as set forth in claim 1, wherein the type of measurement comprises measurement of an amount of total cholesterol, measurement of an amount of High Density Lipoprotein (HDL) cholesterol, and/or measurement of an amount of triglyceride.

6. A method of measuring biomedical data from the measurement strip inserted in the apparatus of claim 1, comprising:
    determining whether the reactive portions are present in the predetermined areas of the measurement strip corresponding to the plurality of respective detection units of the apparatus, based on the detection results obtained by the detection units;
    determining the type of measurement based on results of the determination; and
    measuring the biomedical data based on the type of measurement.

7. The method as set forth in claim 6, further comprising, before determining the type of measurement, determining whether the measurement strip has been inserted based on the detection results obtained by the detection units.

8. The apparatus as set forth in claim 1, wherein the activating of at least one detection unit among the plurality of detection unit is determined by amount of light received from each detection unit.

* * * * *